United States Patent [19]
Bissett

[11] Patent Number: 5,922,758
[45] Date of Patent: Jul. 13, 1999

[54] METHODS AND COMPOSITIONS EMPLOYING 2,4-DIENOIC ACID ESTERS OF TOCOPHEROLS TO PREVENT OR REDUCE SKIN DAMAGE

[75] Inventor: Donald L. Bissett, Hamilton, Ohio

[73] Assignee: The Procter & Gamble Company, Cincinnati, Ohio

[21] Appl. No.: 09/058,620

[22] Filed: Apr. 9, 1998

Related U.S. Application Data

[63] Continuation-in-part of application No. 08/902,868, Jul. 30, 1997, Pat. No. 5,739,156, which is a continuation of application No. 08/309,838, Sep. 21, 1994, abandoned.

[51] Int. Cl.⁶ .................................................. A61K 31/355
[52] U.S. Cl. ............................................................ 514/458
[58] Field of Search ............................................. 514/458

[56] References Cited

U.S. PATENT DOCUMENTS

| | | | |
|---|---|---|---|
| 3,903,297 | 9/1975 | Robert | 424/305 |
| 3,989,816 | 11/1976 | Rhaadhyaksha | 424/60 |
| 4,017,641 | 4/1977 | DiGiulio | 424/365 |
| 4,130,667 | 12/1978 | Smith | 424/361 |
| 4,537,776 | 8/1985 | Cooper | 514/424 |
| 4,552,872 | 11/1985 | Cooper et al. | 514/175 |
| 4,557,934 | 12/1985 | Cooper | 424/128 |
| 4,847,071 | 7/1989 | Bissett et al. | 424/59 |
| 4,847,072 | 7/1989 | Bissett et al. | 424/59 |
| 4,954,487 | 9/1990 | Cooper et al. | 514/159 |
| 5,439,954 | 8/1995 | Bush | 424/59 |
| 5,739,159 | 4/1998 | Bissett | 514/458 |

FOREIGN PATENT DOCUMENTS

| | | | |
|---|---|---|---|
| 0313305 | 4/1989 | European Pat. Off. | A61K 7/40 |
| WO 91/16034 | 10/1991 | WIPO | A61K 7/42 |
| WO 91/16035 | 10/1991 | WIPO | A61K 7/42 |

OTHER PUBLICATIONS

*Remington's Pharmasceutical Sciences,* 17 ed., Chapter 85, p. 1518 (1985).

Buettner et al., :Ascorbate Free Radical as a Marker of Oxidative Stress: An EPR Study, *Free Radical Biology Medicine,* vol. 14 pp.49–55(1993).

*Primary Examiner*—Kimberly Jordan
*Attorney, Agent, or Firm*—Loretta J. Henderson; Milton B. Graff, IV; John M. Howell

[57] ABSTRACT

The subject invention involves methods and compositions for reducing non-ultraviolet-induced free radical damage in mammals comprising administering to a mammal a composition comprising a safe and effective amount of a compound selected from 2,4-dienoic acid esters of tocopherols and mixtures of such compounds, optionally in combination with chelating agents and/or anti-inflammatory agents.

27 Claims, No Drawings

METHODS AND COMPOSITIONS EMPLOYING 2,4-DIENOIC ACID ESTERS OF TOCOPHEROLS TO PREVENT OR REDUCE SKIN DAMAGE

CROSS-REFERENCE TO RELATED APPLICATIONS

This application is a continuation-in-part of the application having U.S. Ser. No. 08/902,868, filed Jul. 30, 1997, now U.S. Pat. No. 5,739,156, issued Apr. 14, 1998, which is in turn a continuation of the application having U.S. Ser. No. 08/309,838, filed Sep. 21, 1994, now abandoned.

FIELD OF THE INVENTION

The subject invention relates to the field of protecting mammalian skin from free radical damage and specific conditions accelerated by free radical damage. In particular, the subject invention relates to novel skin treatment methods and compositions using 2,4-dienoic acid esters of tocopherols for preventing or reducing certain effects of free radicals on mammalian skin.

BACKGROUND OF THE INVENTION

Free radicals, in particular oxygen radicals, in mammalian cells arise from a variety of environmental sources. Such sources include smoke, pollution including ozone and radiation in addition to normal cell metabolism and inflammatory processes. Free radicals are known to be damaging to biological tissue components such as structural proteins, membrane lipids and nucleic acids, resulting in alteration or loss of tissue and cell function, cell death, and cancer. A well recognized source for generation of tissue damaging radicals is radiation, such as UV radiation which causes high levels of radical production in the skin, leading to skin cancer and pre-mature skin aging (skin wrinkling). The use of tocopherol sorbate for preventing ultraviolet-induced damage to skin is disclosed in U.S. Pat. No. 4,847,072 issued to Bissett and Bush on Jul. 11, 1989.

Based on a growing body of evidence, it is believed that free radicals produced as by-products in normal metabolism can cause damage which is responsible for chronological aging of all tissues, including the skin. This has been termed the free radical theory of aging. Such free radicals are often produced by causes other than exposure of tissues to ultraviolet light. Free radicals produced by normal metabolism can cause skin damage, via protein oxidation (also known as glycation) and inflammation.

Nonultraviolet induced free radicals can also cause pigmentation of the skin. This can include post-inflammatory hyperpigmentation that results from acne, insect/spider bites, allergic reactions, irritation from topical materials, drug phototoxicity (from oral or topical drug dosing), infections of bacterial or fungal nature, recovery from injuries such as cuts or blisters, razor bumps (especially from in-grown hairs), and the like.

The mammalian body has a variety of anti-radical defenses, such as small molecule anti-oxidants (e.g., vitamin C, vitamin E, beta-carotene) and anti-oxidant enzymes (e.g., superoxide dismutase, catalase). However, these defenses are often not sufficient to combat the levels or types of radicals produced from environmental or endogenous sources. Therefore, to more completely combat the damaging effects of free radicals, especially oxygen radicals, free radical scavengers and anti-oxidants can be used. These compounds react with the radical species to convert them to stable, non-reactive materials.

It is an object of the present invention to provide methods for reducing nonultraviolet-induced free radical damage in mammalian cells.

It is a further object of the present invention to provide methods for preventing or treating pollution-based skin damage to provide benefits of skin texture protection, barrier protection, prevention of skin sensitivity and prevention of skin dryness.

It is a futher object of the present invention to provide methods for preventing or treating metabolism-induced skin damage to provide benefits of preventing chronological skin aging changes (sagging, sallowness), preventing thinning of the skin (atrophy), and preventing loss of functional blood vessels.

It is a further object of the present invention to provide methods for preventing or treating free radical-induced pigmentation of the skin.

It is a further object of the present invention to provide skin care compositions which can be used to carry out the foregoing methods.

SUMMARY OF THE INVENTION

In its method aspects, the subject invention involves various methods for preventing or treating nonultraviolet-induced free radical damage, inflammation and/or pigmentation in mammalian skin. Such methods generally comprise topically administering to a mammalian skin a composition comprising a safe and effective amount of a compound selected from 2,4-dienoic acid esters of tocopherols, or a mixture of such compounds. Using such methods, actual or potential damage, inflammation and/or hyperpigmentation caused by pollution such as smoke or ozone, normal metabolism-induced radical generation and post-inflammatory effects can be reduced. In its composition aspects, the subject invention relates to skin care compositions comprising safe and effective amounts of the same tocopherol esters used in the methods herein, in combination with safe and effective amounts of chelating agents or anti-inflammatory agents.

DETAILED DESCRIPTION OF THE INVENTION

It has been unexpectedly found that compositions comprising the subject compounds exhibit the ability to reduce levels of free radicals in mammalian tissues. This reduction of the levels of free radicals occurs in mammalian cells which have not experienced substantial recent exposure to ultraviolet light. Exposure to ultraviolet light is known to cause a high level of free radicals to form in mammalian cells. It has surprisingly been found that the subject compounds reduce the levels of free radicals in cells not recently exposed to ultraviolet light to a substantially greater extent than other anti-radical compounds.

While the subject invention is not limited to any particular mode of action, it is believed that the subject compounds may reduce the level of free radicals in mammalian cells by preventing the formation of the most damaging radical species. The subject compounds are believed to react efficiently with the above mentioned radical species. The subject compounds, which act as radical scavengers, are unexpectedly effective against both environmentally induced radical production as well as the endogenous radical production arising from metabolism. The subject compounds are also believed to reduce or prevent the depletion of the natural reserve of Vitamin C in mammalian cells.

As used herein, "alkyl" means a substituted or unsubstituted carbon-containing chain which may be straight or branched, saturated, monounsaturated (i.e., one double or triple bond in the chain), or polyunsaturated (i.e., two or more double bonds in the chain; two or more triple bonds in the chain; one or more double and one or more triple bonds in the chain).

As used herein, "topical application" means directly laying on or spreading on outer skin.

As used herein, "pharmaceutically-acceptable" means that salts, drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors within the knowledge and expertise of the attending physician.

As used herein, "free radical" means an atom or group of atoms that have one or more unpaired electrons. Such atoms or groups of atoms are highly reactive and unstable species. Also included among "free radicals" are other oxygen species which are highly reactive toward biological systems. Some "free radicals" are produced by the catalytic action of metals (e.g., iron or copper) or are more reactive toward biological systems in the presence of metals (e.g., iron or copper). Specific non-limiting examples of "free radicals" as defined above are:

| | |
|---|---|
| superoxide | $O_2^-$ |
| hydroperoxyl radical | $HO_2$ |
| peroxide ion | $O_2^{2-}$ |
| hydroperoxyl anion | $HO_2^-$ |
| hydroxyl radical | $HO$ |
| singlet oxygen | $^1O_2$ |
| hydrogen peroxide | $H_2O_2$ |
| ferryl iron | $FeO^{2+}$ |
| perferryl iron | $FeO_4^{3-}$ |

As used herein, "nonultraviolet-induced free radicals" means free radicals occurring in mammalian cells which are formed in such cells due to conditions other than exposure of the cells to ultraviolet light.

As used herein, "free radical damage" means the alteration in structure, function, composition, or other properties of biological tissues, organs, cells, or constituents that result from the effect of a free radical on them. Since free radicals are highly reactive and unstable species, they will in general react with a wide variety of biological targets to damage them. For example, the oxidation of lipids (lipid peroxidation), especially of cell membrane lipid, is a well-known damaging effect of radicals in biological systems.

ACTIVE AGENT

The subject invention involves a method for protecting mammalian cells from nonultraviolet-induced free radical damage by reducing the level of free radicals in mammalian cells by administering to the mammal a safe and effective amount of a compound selected from 2,4-dienoic acid esters of tocopherols or a mixture of such compounds (mixed isomers).

As used herein, "tocopherols" include compounds having the following structure:

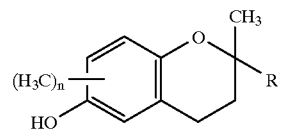

wherein n is an integer selected from 0, 1, 2 and 3; and R is

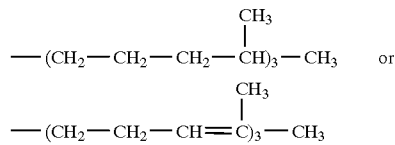

Preferred n is 2 or 3, especially 3.
Preferred R is

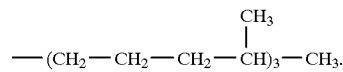

Preferred tocopherols which are subject compounds are naturally-occurring tocopherols including the following:
alpha-tocopherol (Vitamin E) having the structure:

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

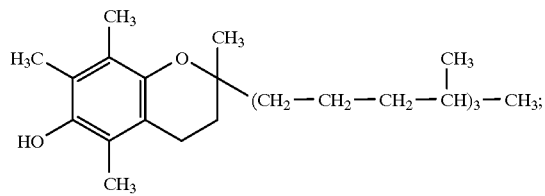

beta-tocopherol having the structure:

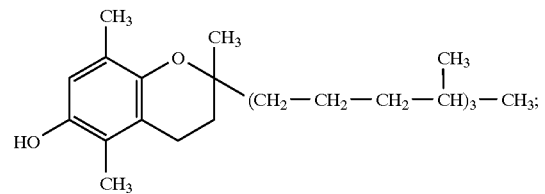

gamma-tocopherol having the structure:

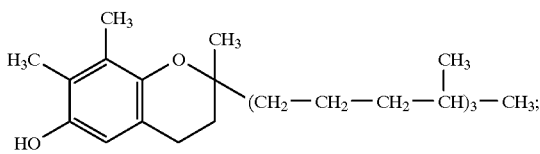

delta-tocopherol having the structure:

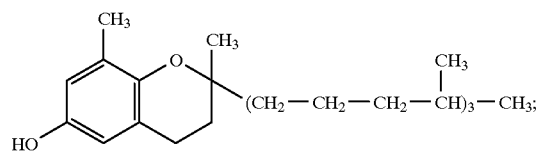

epsilon-tocopherol having the structure:

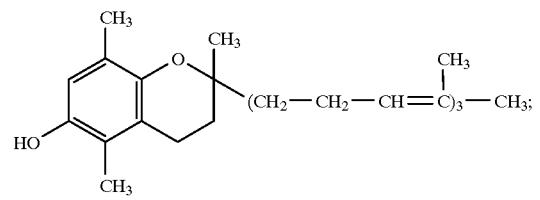

zeta₁-tocopherol having the structure:

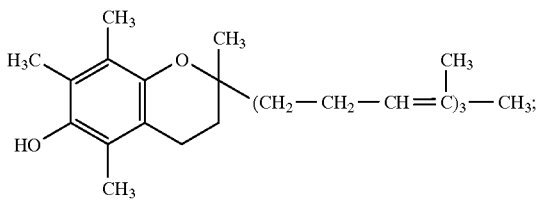

zeta₂-tocopherol having the structure:

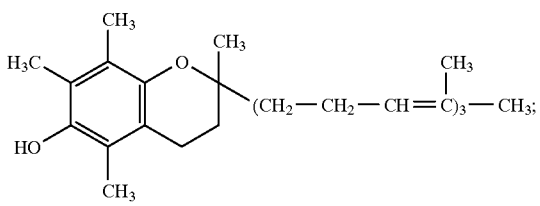

eta-tocopherol having the structure:

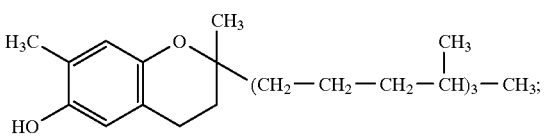

Tocopherols often occur naturally as mixtures of some or all of the above compounds.

Also preferred tocopherols which are part of the subject compounds are synthetic tocopherols.

Preferred synthetic tocopherols which are subject compounds include the following:

tocol having the structure:

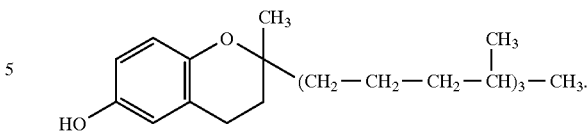

Other tocopherols shown above as naturally-occurring can also be made synthetically, especially alpha-tocopherol and delta-tocopherol.

As used herein, "2,4-dienoic acids" include compounds having the following structure:

R'—CH=CH—CH=CH—COOH wherein R' is hydrogen or alkyl having from 1 to about 7 carbon atoms. Preferred R' is unsubstituted. Preferred R' is saturated. Preferred R' is straight chain. Preferred R' is $C_1$–$C_3$ alkyl, especially methyl. Preferred R' is also $C_2$–$C_7$ alkyl, more preferred is $C_2$–$C_5$ alkyl, more preferred still is $C_2$–$C_3$ alkyl.

The most preferred 2,4-dienoic acid which is part of the subject compounds is sorbic acid:

CH₃—CH=CH—CH=CH—COOH

The subject invention compounds are esters where the above 2,4-dienoic acids are esterified with the hydroxy moiety at the 6-position of the benzopyran-6-ol ring of the above tocopherols.

Preferred active compounds of the subject invention include alpha-tocopherol sorbate, tocol sorbate, delta-tocopherol sorbate, and tocopherol (mixed isomers) sorbate. The most preferred compound of the subject invention is alpha-tocopherol sorbate.

Safe and effective amounts of the tocopherol esters used in this invention can include, for example, concentrations of from about 0.1% to 10% by weight of compositions containing these materials. Preferred concentrations for the tocopherol esters range from about 0.5% to 2% by weight of compositions containing them.

COMBINATION ACTIVES

A. Sunscreens and Sunblocks

Reduction of the level of free radicals in mammalian cells can be achieved by using combinations of the subject compounds together with sunscreens or sunblocks. A known inducer of free radicals is ultraviolet radiation. Thus, in topical compositions, the inclusion of sunscreens/sunblocks would increase protection against radical production and subsequent damage. Useful sunblocks include, for example, zinc oxide and titanium dioxide. The combination of an active agent, with a UVA and/or UVB sunscreen is desirable. The inclusion of sunscreens in compositions useful in the subject invention at low levels does not greatly reduce the tanning response of the user but enhances the effectiveness of the subject compositions. A wide variety of conventional sunscreening agents are suitable for use in combination with a subject active agent. Sagarin, et al., at Chapter VIII, pages 189 et seq., of *Cosmetics Science and Technology,* disclose numerous suitable agents.

A safe and effective amount of sunscreen may be used in the compositions useful in the subject invention. The sunscreening agent must be compatible with the active agent. The composition preferably comprises from about 1% to about 20%, more preferably from about 2% to about 10% of a sunscreening agent. Exact amounts will vary depending upon the sunscreen chosen and the desired Sun Protection Factor.

B. Anti-Inflammatory Agents

In a preferred composition useful in the subject invention, an anti-inflammatory agent is included as an active along with a subject compound. The inclusion of an anti-inflammatory agent enhances the benefits of the compositions because the mammalian body will respond to radical damage by mounting an inflammation response which can lead to additional cell damage. The anti-inflammatory agent also protects strongly in the UVA radiation range (though it also provides some UVB protection as well). (See U.S. Pat. No. 4,847,071, Bissett, Bush, and Chatterjee, issued Jul. 11, 1989, incorporated herein by reference; and U.S. Pat. No. 4,847,069, Bissett and Chatterjee, issued Jul. 11, 1989, incorporated herein by reference.) Preferred anti-inflammatory agents include naproxen, ibuprofen, flufenamic acid, hydrocortisone and etofenamate.

A safe and effective amount of an anti-inflammatory agent may be added to the compositions useful in the subject invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

C. Chelators

In a preferred composition useful in the subject invention, a chelating agent is included as an active along with a subject compound. As used herein, "chelating agent" means an active agent capable of removing a metal ion from a system by forming a complex so that the metal ion cannot readily participate in or catalyze chemical reactions. The inclusion of a chelating agent increases the benefits of the composition.

A safe and effective amount of a chelating agent may be added to the compositions useful in the subject invention, preferably from about 0.1% to about 10%, more preferably from about 1% to about 5%, of the composition. Chelators useful in compositions are disclosed in U.S. Pat. Nos. 5,487,884; 5,462,963 and 5,364,617 and in U.S. patent application Ser. No. 07/776,506, Bush, filed Oct. 11, 1991 (P&G Case 4507). All of these patent documents are incorporated herein by reference.

The preferred chelators include:
kojic acid
2,3-bis-(2-pyridyl)-pyrazine
3-(4-phenyl-2-pyridyl)-5-phenyl-1,2,4-triazine
2,3-bis-(2-pyridyl)-5,6-dihydropyrazine
2,4,6-tri-(2-pyridyl)-1,3,5-triazine
1-pyrrolidine carbodithioic acid
di-2-pyridyl ketone
phenyl 2-pyridyl ketoxime
2,3-dihydroxy naphthalene
2,3-dihydroxy pyridine
3-hydroxy-2-methyl-4-pyrone
2,3-dihydroxy benzoic acid
ethylenediamine-N,N-bis-(2-hydroxy-phenylacetic acid) dimethyl ester
2-furildioxime
2-furilmonoxime
1-phenyl-1,2-propanedione-2-oxime
1-phenyl-1,3-butanedione
1-hydroxy-4-methyl-t-(2,4,4-trimethyl-pentyl)-2(1H)-pyridinone
diethyidithiocarbamic acid
deferoxamine
1,2-dimethyl-3-hydroxypyrid-4-one In a preferred composition useful in the subject invention, compositions comprise one, any two, or all three of a sunscreening agent, anti-inflammatory agent, and/or chelating agent included as actives along with the subject active agent. The inclusion of two, or all three of these agents with the active agent increases the benefits of the composition.

METHODS FOR REDUCING FREE RADICAL DAMAGE IN MAMMALIAN CELLS

The subject invention relates to methods for reducing the level of free radicals in mammalian cells. The reduction of the level of free radicals in mammalian cells reduces the level of free radical aging in the cells.

The level of free radicals in mammalian cells can be determined experimentally using radical traps. Methods for EPR (electron paramagnetic resonance) analysis of radicals in the skin include the following:

Female albino Skh:HR-1 hairless mice are treated topically 3 times per week (e.g., Monday, Wednesday, and Friday) on the dorsal skin surface with 0.1 ml of test material in isopropanol or with isopropanol alone. The skin is then analyzed in vitro in an EPR instrument (Bruker ESP 300 spectrometer, Bruker Instruments, Karlsruhe, Germany) for level of radicals using two radical traps: (1) endogenous ascorbate in which the skin's endogenous ascorbic acid serves as the trap and ascorbyl radical is detected; and (2) exogenous POBN (alpha-(4-pyridyl-1-oxide)-N-tert-butyl nitrone) in which 0.05 ml of 250 mM POBN is applied to the skin sample surface for 10 minutes prior to analysis in the EPR. The skin samples are then placed in a tissue cell (Wilmad Glass Co., Buena, N.J.) and positioned in the EPR cavity.

The above ascorbyl radical method is non-specific in that a wide range of radicals generated in the skin are trapped by ascorbate. This method is described in the following reference: Buettner, G. R., and B. A. Jurkiewicz, "Ascorbate Free Radical as a Marker of Oxidative Stress: An EPR Study", *Free Radical Biology & Medicine,* Vol. 14 (1993), pp. 49–55.

The above POBN method captures a carbon-centered lipid radical and thus more specifically traps lipid oxidation radicals. The measurement is made at room temperature using the EPR instrument. The POBN radical adduct gives a triplet of doublets signal. Only the first doublet signal height is measured for each experiment; there is no interference from other signals for this first doublet. The EPR settings are: microwave power, 40 milliwatts; modulation amplitude, 0.75 G; time constant, 0.3 sec; scan rate, 60 G/41.9 sec; receiver gain, $1\times10^6$.

The subject methods for reducing nonultraviolet-induced free radical damage in mammalian cells involve administration of a safe and effective amount of a subject compound. The amount of compound administered and frequency of administration will vary widely depending upon the conditions of the cells already in existence in the subject and the level of treatment desired.

The preferred modes of administration are topically, and parenterally (for example, by subcutaneous injection, intramuscular injection, and the like). Thus, specific modes of administration include, without limitation, transdermal, mucosal, and subcutaneous administration, as well as topical application.

Compositions of the subject invention are preferably administered topically to a mammal by the direct laying on or spreading of the composition on the skin. Topical compositions comprising tocopherol sorbate are disclosed in U.S. Pat. No. 4,847,072 issued to Bissett and Bush Jul. 11, 1989, which is hereby incorporated herein by reference. Other compounds of the subject invention can be substituted for tocopherol sorbate in such compositions.

The topical compositions useful in the subject invention involve compositions suitable for topical application to mammalian skin, the composition comprising a safe and effective amount of an active compound or mixture of such actives as described hereinabove, and a pharmaceutically-acceptable topical carrier. The subject compositions preferably contain from about 0.001% to about 20%, more preferably from about 0.01% to about 15%, more preferably still from about 0.1% to about 10%, also preferably from about 0.5% to about 2%, also preferably from about 1% to about 5%.

The topical compositions useful in the subject invention may be made into a wide variety of product types. These include, but are not limited to lotions, creams, beach oils, gels, sticks, sprays, ointments, pastes, mousses, cosmetics, shampoos, cream rinses, hair tonics and hair conditioners. These product types may comprise several types of carrier systems including, but not limited to solutions, emulsions, gels, solids, and liposomes. Topical compositions preferably comprise from about 1% to about 50%, more preferably from about 5% to about 25% of an emollient.

The topical compositions useful in the subject invention may include a safe and effective amount of penetration enhancing agent. A preferred amount of penetration enhancing agent is from about 1% to about 5% of the composition. Examples of useful penetration enhancers, among others, are disclosed in U.S. Pat. Nos. 4,537,776, Cooper, issued Aug. 27, 1985; 4,552,872, Cooper et al., issued Nov. 12, 1985; 4,557,934, Cooper, issued Dec. 10, 1985; 4,130,667, Smith, issued Dec. 19, 1978; 3,989,816, Rhaadhyaksha, issued Nov. 2, 1976; 4,017,641, DiGiulio, issued Apr. 12, 1977; and 4,954,487, Cooper, Loomans & Wickett, issued Sep. 4, 1990.

Other skin care product additives may also be included in the compositions useful in the subject invention. For example, collagen, hyaluronic acid, salicylic acid, phytic acid, hydroxyquinone, arbutin compounds, elastin, hydrolysates, primrose oil, jojoba oil, epidermal growth factor, soybean saponins, mucopolysaccharides, and mixtures thereof may be used.

Various vitamins may also be included in the compositions useful in the subject invention. For example, vitamin A, and derivatives thereof, vitamin $B_2$, biotin, pantothenic acid, vitamin D, and mixtures thereof may be used.

A safe and effective amount of active agent, in a topical composition, is applied, generally from about 0.001 mg to about 2 mg per $cm^2$ skin per application, preferably from about 0.005 mg to about 1 mg per $cm^2$ skin per application, more preferably from about 0.01 mg to about 0.5 mg/$cm^2$, also preferably from about 0.02 mg to about 0.2 mg/$cm^2$. Application preferably ranges from about weekly to about 5 times daily, more preferably from about twice a week to about four times daily, more preferably still from about every other day to about 3 times daily, also preferably from about once a day to about twice a day. The subject compositions are preferably applied to an area of from about 10 $cm^2$ to about 10,000 $cm^2$ skin for each application, more preferably from about 100 $cm^2$ to about 5,000 $cm^2$ skin, also preferably from about 500 $cm^2$ to about 1000 $cm^2$ skin. Treatment is continued for at least 7 days, more preferably 6 months, even more preferably 1 year, more preferably still 5 years, also preferably 10 years.

A preferred method of the subject invention involves applying both a safe and effective amount of a subject compound and a safe and effective amount of one or more of a sunscreening agent, an anti-inflammatory agent, and/or a chelating agent, to the skin simultaneously. As used herein, "simultaneous application" or "simultaneously" means applying the agents to the skin at the same situs on the body at about the same time. Though this can be accomplished by applying the agents separately to the skin, preferably a composition comprising all the desired agents commingled is applied to the skin. The amount of sunscreening agent applied is preferably from about 0.05 mg to about 0.5 mg per $cm^2$ skin. The amount of anti-inflammatory agent applied is preferably from about 0.005 mg to about 0.5 mg, more preferably from about 0.01 mg to about 0.1 mg per $cm^2$ skin. The amount of chelating agent preferably applied is from about 0.001 mg to about 1.0 mg, more preferably from about 0.01 mg to about 0.5 mg, still more preferably from about 0.05 mg to about 0.1 mg per $cm^2$ skin. The amount of the active compound of the subject invention applied is preferably from about 0.001 mg to about 2 mg per $cm^2$ skin per application, more preferably from about 0.01 mg to about 0.5 mg per $cm^2$ skin per application.

EXAMPLES

The following examples further describe and demonstrate embodiments within the scope of the subject invention. The examples are given solely for the purpose of illustration and are not to be construed as limitations of the subject invention, as many variations thereof are possible without departing from the spirit and scope of the invention.

Example 1

A topical composition is prepared by combining the following components utilizing conventional mixing techniques.

| Component | % Weight |
|---|---|
| Isopropanol | 98 |
| Alpha-tocopherol sorbate | 2 |

In a suitable vessel, the alpha-tocopherol sorbate is dissolved in the isopropanol with stirring. Use of an amount of the composition to deposit about 0.02 mg/$cm^2$ of the alpha-tocopherol sorbate to about 200 $cm^2$ of skin is appropriate. The composition is applied twice daily, for a period of five years.

Example 2

A topical composition is prepared by combining the following components utilizing conventional mixing techniques.

| Component | % Weight |
|---|---|
| Ethanol | 99.5 |
| Tocol sorbate | 0.5 |

In a suitable vessel, the tocol sorbate is dissolved in the ethanol with stirring. Use of an amount of the composition to deposit about 0.001 mg/cm$^2$ of the tocol sorbate to the skin is appropriate. The composition is applied four times daily over a 1000 cm$^2$ area of skin for a period of six months.

Example 3

A topical composition is prepared by combining the following components utilizing conventional mixing techniques.

| Component | % Weight |
|---|---|
| Ethanol | 49.00 |
| Propylene glycol | 25.00 |
| Deionized water | 25.00 |
| Tocopherol (mixed isomers) sorbate | 1.00 |

In a suitable vessel, the tocopherol sorbate is dissolved in the ethanol with stirring. Propylene glycol and deionized water are added with stirring. Use of an amount of the composition to deposit about 0.02 mg/cm$^2$ of the gamma-tocopherol 2,4-octadienoate to 2000 cm$^2$ of skin is appropriate. The composition is applied once a week for one year.

Example 4

A nonionic oil-in-water emulsion is prepared by combining the following components utilizing conventional mixing techniques:

| Component | % Weight |
|---|---|
| Deionized water | 78.73 |
| Propylene glycol | 3.00 |
| Octyl methoxycinnamate | 7.50 |
| Cetyl alcohol | 2.50 |
| Stearyl alcohol | 2.50 |
| Laureth 23 | 2.00 |
| C$_{12-15}$ alcohols benzoate | 2.00 |
| EDTA | 0.37 |
| Methylparaben | 0.20 |
| Propylparaben | 0.10 |
| Delta-tocopherol sorbate | 1.10 |

Use of an amount of the composition sufficient to deposit about 0.004 mg/cm$^2$ skin of the delta-tocopherol sorbate is appropriate. The composition is applied twice a week to about 500 cm$^2$ of skin for two years.

Example 5

A nonionic oil-in-water emulsion is prepared by combining the following components utilizing conventional mixing techniques:

| Component | % Weight |
|---|---|
| Deionized water | 78.73 |
| Propylene glycol | 3.00 |
| Octyl methoxycinnamate | 7.50 |
| Cetyl alcohol | 2.50 |
| Stearyl alcohol | 2.50 |
| Laureth 23 | 2.00 |
| C$_{12-15}$ alcohols benzoate | 2.00 |
| EDTA | 0.37 |
| Methylparaben | 0.20 |
| Propylparaben | 0.10 |
| Alpha-tocopherol sorbate | 1.10 |

Use of an amount of the composition sufficient to deposit about 0.05 mg/cm$^2$ of the alpha-tocopherol sorbate to about 100 cm$^2$ of skin is appropriate. The composition is applied once daily, for three years.

Example 6

An oil-in-water emulsion is prepared by combining the following components utilizing conventional mixing techniques.

| Component | % Weight |
|---|---|
| Deionized water | 78.05 |
| Permulon TR-2 (C10–C30 acrylate copolymer, B. F. Goodrich) | 0.30 |
| Distearyl dimethyl ammonium chloride | 0.15 |
| Tocol sorbate | 1.00 |
| 4-N,N-(2-ethylhexyl)methylaminobenzoic acid 4-ester of 2-hydroxy-4-(2-hydroxyethpxy)-benzophenone | 4.00 |
| 4-N,N-(2-ethylhexyl)methylaminobenzoic acid ester of 4-(2-hydroxyethoxy)dibenzoylmethane | 2.00 |
| Dimethyl isosorbide | 6.00 |
| Dioctyl malate | 6.00 |
| Cetyl alcohol | 1.00 |
| Stearyl alcohol | 1.00 |
| 99% triethanolamine | 0.50 |

Use of an amount of the composition sufficient to deposit about 0.1 mg/cm$^2$ of the tocol sorbate to about 1000 cm$^2$ of skin is appropriate. The composition is applied twice daily, for one year.

Example 7

A sunscreen composition is prepared by combining the following components utilizing conventional mixing techniques.

| Component | % Weight |
|---|---|
| Polypropylene glycol 15 stearyl ether | 15.00 |
| Sorbitan oleate | 2.00 |
| Octyl methoxy cinnamate | 7.50 |
| 2-furildioxime | 0.50 |
| Tocopherol (mixed isomers) sorbate | 1.00 |
| Propyl paraben | 0.15 |
| Butylated hydroxy toluene | 0.05 |
| Cyclomethicone | 20.00 |
| Sesame oil | 5.00 |
| Mineral oil (Blandol) | 48.8 |

Use of an amount of the composition is sufficient to deposit about 0.1 mg/cm2 of the tocopherol sorbate to the skin is appropriate. This composition is applied three times daily, for six months.

Example 8

A topical composition is prepared by combining the following components using conventional mixing techniques.

| Component | Weight % |
|---|---|
| Water | 69.363 |
| Tetrasodium EDTA | 0.020 |
| Glycerine | 3.000 |
| Triethanolamine | 0.100 |
| Fluid AP | 6.000 |
| Parsol 1789 | 3.000 |
| Parsol MCX | 7.500 |
| Ganex V220 | 0.500 |
| Stearly alcohol | 1.000 |
| Cetyl alcohol | 1.000 |
| Brij 721 | 0.531 |
| Brij 72 | 0.286 |
| Dimethicone gum | 0.500 |
| Salicylic acid | 2.000 |
| Salcare SC-95 | 2.000 |
| Alpha-tocopherol sorbate | 1.000 |
| Oxybenzone | 1.000 |
| Silicone DC 1403 | 1.000 |
| Fragrance | 0.200 |

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. A method of preventing or treating ozone, smoke and/or pollution damage to mammalian skin, which method comprises topically applying to mammalian skin at risk of or subjected to such damage a composition comprising a safe and effective amount of a compound selected from 2,4-dienoic acid esters of tocopherols and mixtures of such compounds.

2. The method of claim 1 wherein the 2,4-dienoic acid esters of tocopherols have the following structure:

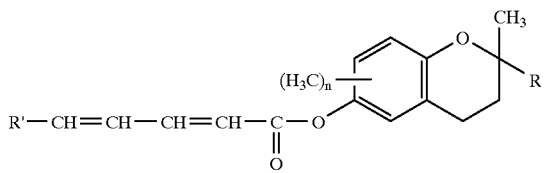

wherein:

(a) n is an integer from 0 to 3;
(b) R is

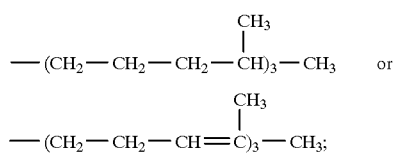

and (c) R' is hydrogen or alkyl having from 1 to about 7 carbon atoms.

3. The method of claim 2 wherein R' is saturated and unsubstituted.

4. The method of claim 3 wherein R' is $C_1$–$C_3$ alkyl.
5. The method of claim 2 wherein R' is hydrogen.
6. The method of claim 2 wherein R' is $C_2$–$C_7$ alkyl.
7. The method of claim 2 wherein the tocopherols are selected from the group consisting of alpha-tocopherol, beta-tocopherol, gamma tocopherol, delta-tocopherol, epsilon-tocopherol, zeta$_2$-tocopherol, zeta$_1$-tocopherol, eta-tocopherol, and mixtures thereof.
8. The method of claim 2 wherein the tocopherols comprise tocol.
9. The method of claim 7 wherein the composition is applied topically to the skin of a human wherein the amount of the compound applied to the skin is from about 0.01 mg to about 0.5 mg per $cm^2$ skin, from about twice a week to about four times a day, for a period of one week or more.
10. A method of preventing or treating normal metabolism radical induced damage and inflammation to mammalian skin, which method comprises topically applying to mammalian skin which is suceptible to such damage and inflammation a composition comprising a safe and effective amount of a compound selected from 2,4-dienoic acid esters of tocopherols and mixtures of such compounds.
11. The method of claim 10 wherein the 2,4-dienoic acid esters of tocopherols have the following structure:

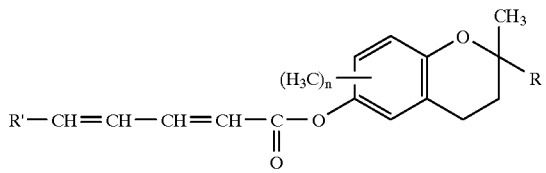

wherein:

(a) n is an integer from 0 to 3;
(b) R is

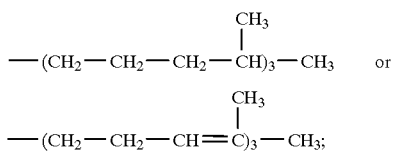

and (c) R' is hydrogen or alkyl having from 1 to about 7 carbon atoms.

12. The method of claim 11 wherein R' is saturated and unsubstituted.
13. The method of claim 12 wherein R' is $C_1$–$C_3$ alkyl.
14. The method of claim 11 wherein R' is hydrogen.
15. The method of claim 11 wherein R' is $C_2$–$C_7$ alkyl.
16. The method of claim 11 wherein the tocopherols are selected from the group consisting of alpha-tocopherol, beta-tocopherol, gamma tocopherol, delta-tocopherol, epsilon-tocopherol, zeta$_2$-tocopherol, zeta$_1$-tocopherol, eta-tocopherol, and mixtures thereof.
17. The method of claim 11 wherein the tocopherols comprise tocol.
18. The method of claim 16 wherein the composition is applied topically to the skin of a human wherein the amount of the compound applied to the skin is from about 0.01 mg to about 0.5 mg per $cm^2$ skin, from about twice a week to about four times a day, for a period of one week or more.

19. A method of preventing or treating non-ultraviolet free radical induced hyperpigmention of mammalian skin, which method comprises topically applying to mammalian skin at risk of or inflicted with hyperpigmentation a composition comprising a safe and effective amount of a compound selected from 2,4-dienoic acid esters of tocopherols and mixtures of such compounds.

20. The method of claim 19 wherein the 2,4-dienoic acid esters of tocopherols have the following structure:

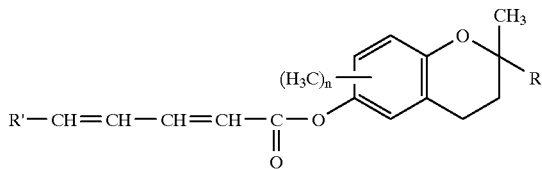

wherein:

(a) n is an integer from 0 to 3;
R is

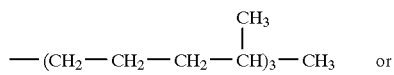  or

-continued

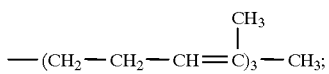

and (c) R' is hydrogen or alkyl having from 1 to about 7 carbon atoms.

21. The method of claim 20 wherein R' is saturated and unsubstituted.

22. The method of claim 21 wherein R' is $C_1$–$C_3$ alkyl.

23. The method of claim 20 wherein R' is hydrogen.

24. The method of claim 20 wherein R' is $C_2$–$C_7$ alkyl.

25. The method of claim 20 wherein the tocopherols are selected from the group consisting of alpha-tocopherol, beta-tocopherol, gamma tocopherol, delta-tocopherol, epsilon-tocopherol, $zeta_2$-tocopherol, $zeta_1$-tocopherol, eta-tocopherol, and mixtures thereof.

26. The method of claim 20 wherein the tocopherols comprise tocol.

27. The method of claim 25 wherein the composition is applied topically to the skin of a human wherein the amount of the compound applied to the skin is from about 0.01 mg to about 0.5 mg per $cm^2$ skin, from about twice a week to about four times a day, for a period of one week or more.

* * * * *